United States Patent [19]

Doll et al.

[11] Patent Number: 4,584,285
[45] Date of Patent: Apr. 22, 1986

[54] ANTIHYPERTENSIVE AGENTS

[75] Inventors: Ronald J. Doll, Maplewood; Bernard R. Neustadt, West Orange; Elizabeth M. Smith; Charles V. Magatti, both of Verona; Elijah H. Gold, West Orange, all of N.J.

[73] Assignee: Schering Corporation, Kenilworth, N.J.

[21] Appl. No.: 651,378

[22] Filed: Sep. 17, 1984

Related U.S. Application Data

[63] Continuation-in-part of Ser. No. 500,494, Jun. 2, 1983, abandoned.

[51] Int. Cl.$^4$ ............... A61K 37/00; C07C 103/52; C07D 409/00; C07D 209/02; C07D 209/04; C07D 209/42; C07D 209/96; C07D 285/16; C07D 217/00; C07D 215/00; C07D 209/44; C07D 209/34

[52] U.S. Cl. .................. 514/19; 260/112.5 R; 260/330.3; 514/278; 514/307; 514/311; 514/228; 514/409; 514/419; 514/423; 546/147; 546/164; 546/165; 544/8; 548/465; 548/468; 548/470; 548/487; 548/491; 548/493; 548/409

[58] Field of Search .................. 260/112.5 R, 330.3; 514/19, 278, 307, 311, 228; 546/147, 164, 165; 544/8; 548/465, 468, 470, 487, 491, 492, 409

[56] References Cited

U.S. PATENT DOCUMENTS 4,374,829  2/1983  Harris et al. ............. 260/112.5 R

FOREIGN PATENT DOCUMENTS 0050800  5/1982  European Pat. Off. ..... 260/112.5 R Primary Examiner—Delbert R. Phillips
Attorney, Agent, or Firm—Anita W. Magatti; Stephen I. Miller

[57] ABSTRACT (Benzothiadiazine, benzamido and benzenesulfonyl)-phenyl-substituted carboxyalkyl dipeptide compounds are disclosed. Compounds of this invention are useful as antihypertensive agents.

27 Claims, No Drawings

ANTIHYPERTENSIVE AGENTS

CROSS REFERENCE TO RELATED APPLICATION

This application is a continuation in part of pending application Ser. No. 500,494 filed June 2, 1983, now abandoned.

SUMMARY

The present invention relates to (benzothiadiazine, benzamido, and benzenesulfonyl)-phenyl-substituted carboxyalkyl dipeptide compounds which have antihypertensive activity. Compounds of this invention are useful as antihypertensive agents, in the treatment of congestive heart failure and glaucoma. In addition, compounds of this invention are useful as diuretics.

DETAILED DESCRIPTION

More particularly, this invention relates to compounds represented by the following formula:

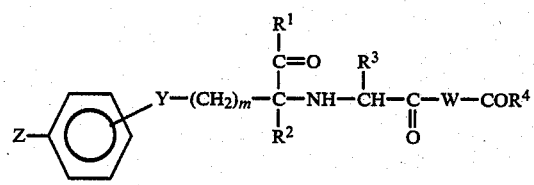

wherein W is

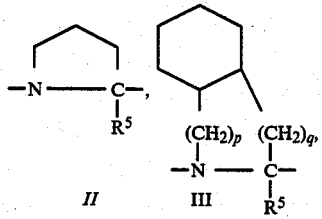

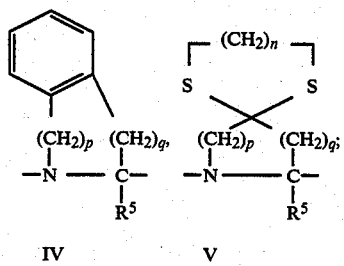

n is 0 or 1;
m is 0 to 2
p and q are each 0, 1 or 2, provided that the sum of p and q is 1 or 2, and that in formula V, p is not 0;
Y is —CH$_2$—, —CH$_2$O—, or —CH$_2$S—, attached at the 2 or 4 position of the phenyl group;
Z is

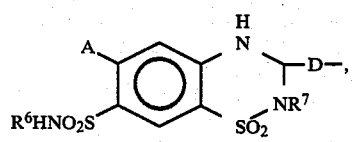

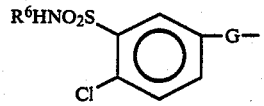

wherein A is Cl or CF$_3$;
D is —(CH$_2$)$_u$—, —CH$_2$O—, —CH$_2$S—;

G is —CONR$^7$(CH$_2$)$_t$—, or —SO$_2$NR$^7$(CH$_2$)$_t$—;
t is 0 or 1;
R$^1$ and R$^4$ are independently hydroxy, alkoxy having from 1 to 8 carbon atoms, K—X$_r$—(CH$_2$)$_s$—O—, wherein K is phenyl, substituted phenyl, 1- or 2-naphthyl, X is oxygen or sulfur, r is 0 or 1 and s is 0 or 4, and wherein the substitutents on the phenyl are chosen from group M, wherein M is halogen, hydroxy, trifluoromethyl, alkoxy having from 1 to 6 carbon atoms, alkyl from 1 to 6 carbon atoms, 2- and 3-furanyl, 2- and 3-thienyl and phenyl (which phenyl group may be substituted with halogen, hydroxy, trifluoromethyl, alkoxy having from 1 to 6 carbon atoms or alkyl having from 1 to 6 carbon atoms), provided that when s is zero, r is zero, —OCH$_2$—OCO-alkyl wherein the alkyl has from 3 to 8 carbon atoms, —OCH$_2$CO— phenyl, wherein the phenyl may be substituted with group M, 1-glyceryl,

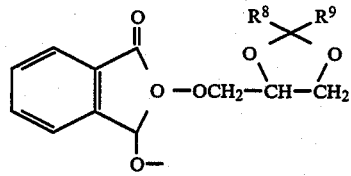

R$^2$, R$^5$, R$^6$ and R$^9$ are hydrogen or lower alkyl;
R$^3$ is hydrogen, lower alkyl or amino lower alkyl;
R$^7$ is hydrogen, lower alkyl or phenyl(lower)alkyl;
R$^8$ is hydrogen, lower alkyl, phenyl, or phenyl substituted by group M;
u is 1 or 2; and the pharmaceutically acceptable salts thereof.

Preferred compounds of the invention are those wherein W is represented by formula III, IV or V. When W is of formula III or IV, preferred values for p and q are 0 and 1, respectively; when W is of formula V, preferred values of p, q and n are 1, 1 and 0 respectively.

Two additional groups of preferred compounds are that wherein R$^2$ and R$^5$ are hydrogen, and that wherein R$^4$ is hydroxy.

Particularly preferred compounds are those wherein W is represented by formula III or V; n, p, q, Y, R$^2$, and R$^5$ are as defined above for preferred compounds; R$^3$ is methyl or amino butyl; Z is of formula VI, wherein A is chlorine, or Z is of formula VII and G is —CONH—CH$_2$— or —SO$_2$NH—CH$_2$; R$^6$ and R$^7$ are hydrogen or methyl; and R$^1$ is hydroxy, ethoxy, methoxy, phenoxyethoxy, or pivaloyloxymethoxy.

As used herein, "lower alkyl" means straight or branched chain hydrocarbon radicals of from 1 to 6 carbons, e.g. methyl, ethyl, propyl, ispropyl, butyl, t-butyl, pentyl and hexyl. Similarly, "lower alkoxy"

means straight or branched alkoxy radicals having 1 to 6 carbon atoms, e.g. methoxy, ethoxy, propoxy, butoxy, iso-butoxy, pentoxy and hexyloxy. "Halogen" means fluorine, chlorine and bromine.

Compounds of the instant invention include various stereoisomers. Preferred stereoisomers are those in which the absolute configuration at each of the three carbon atoms adjacent to both a nitrogen and a carbonyl group corresponds most closely to the absolute configuration of L-amino acids.

The compounds of this invention form salts with various inorganic and organic acids and bases which are also within the scope of the invention. Such salts include ammonium salts, alkali metal salts, e.g. sodium and potassium salts, and alkaline earth metal salts, e.g. calcium and magnesium salts. Salts with organic and inorganic acids may be prepared, e.g., HCl, HBr, $H_2SO_4$, $H_3PO_4$, methanesulfonic acid, toluenesulfonic acid, maleic acid, fumaric acid and camphorsulfonic acid. The nontoxic pharmaceutically acceptable salts are preferred, although other salts are also useful, e.g., in isolating or purifying the product. The acid salts (e.g. HCl and maleate) are preferred, especially the hydrochloride.

The salts may be formed by conventional means, as by reacting the free acid or base forms of the product with one or more equivalents of the appropriate base or acid in a solvent or medium in which the salt is insoluble, or in a solvent such as water which is then removed in vacuo or by exchanging the cations of an existing salt for another cation on a suitable ion exchange resin.

Compounds of formula I may be prepared by several routes using methods known in the art.

For example, compounds of formula I may be prepared by condensing an amino acid of formula VIII with a keto compound of formula IX in the presence of a reducing agent such as sodium cyanoborohydride in a solvent such as ethanol:

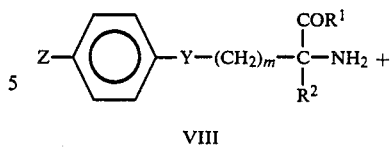

VIII

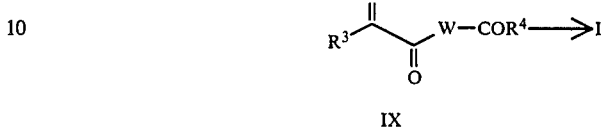

IX wherein Z, Y, $R^1$, $R^2$, $R^3$, $R^4$, m and W are as defined above.

Starting materials of formula VIII may be prepared by well known methods. An example of such a preparation is shown below, wherein 5-(4-[6-chloro-7-sulfamoyl-3,4-dihydro-1,1-dioxo-1,2,4-benzothiadiazinyl-3-)methoxy]benzyl)cysteine (formula XVI) is prepared, starting with 2-bromo-1,1-diethoxyethane and p-cresol:

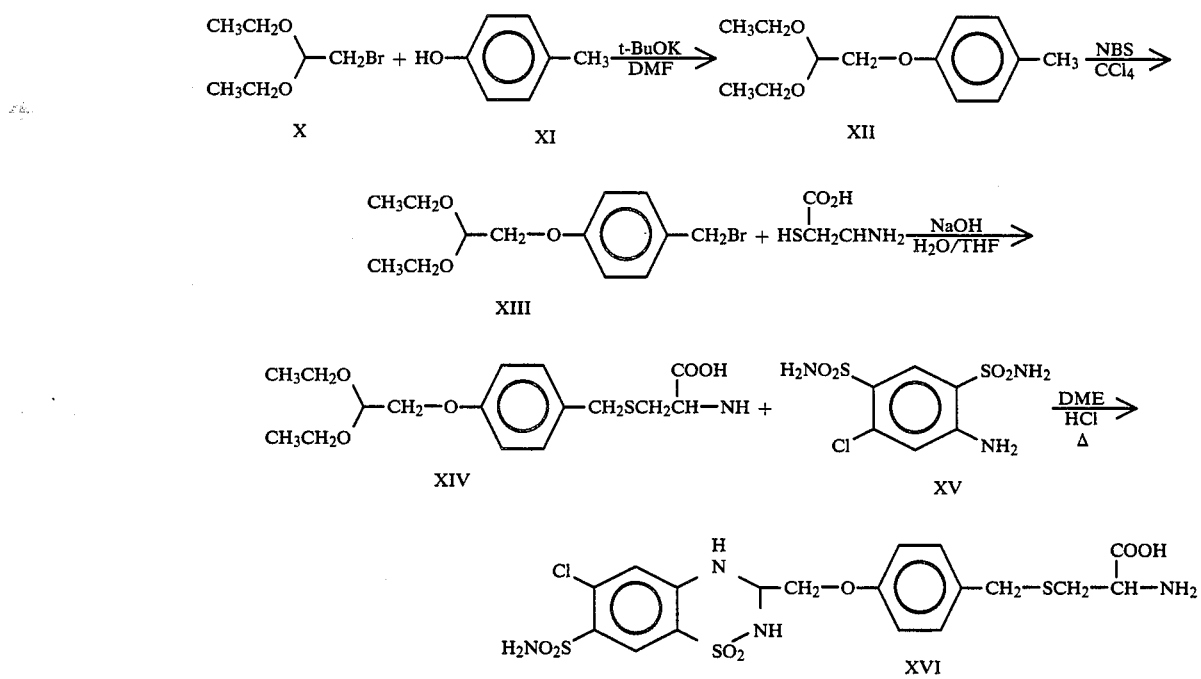

Starting materials of formula IX may be prepared by reacting an amino acid derivative XVIII with an α-keto acid chloride XVII to give the substituted amino acid:

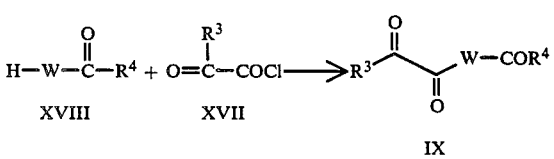

The reaction is carried out in an inert solvent such as methylene chloride in the presence of a base such as triethylamine or pyridine.

Compounds of formula I wherein Y is —$CH_2$—, and Z is a group of formula VII, are preferably prepared by the reaction of an acid of formula XIX with an amine of formula XX:

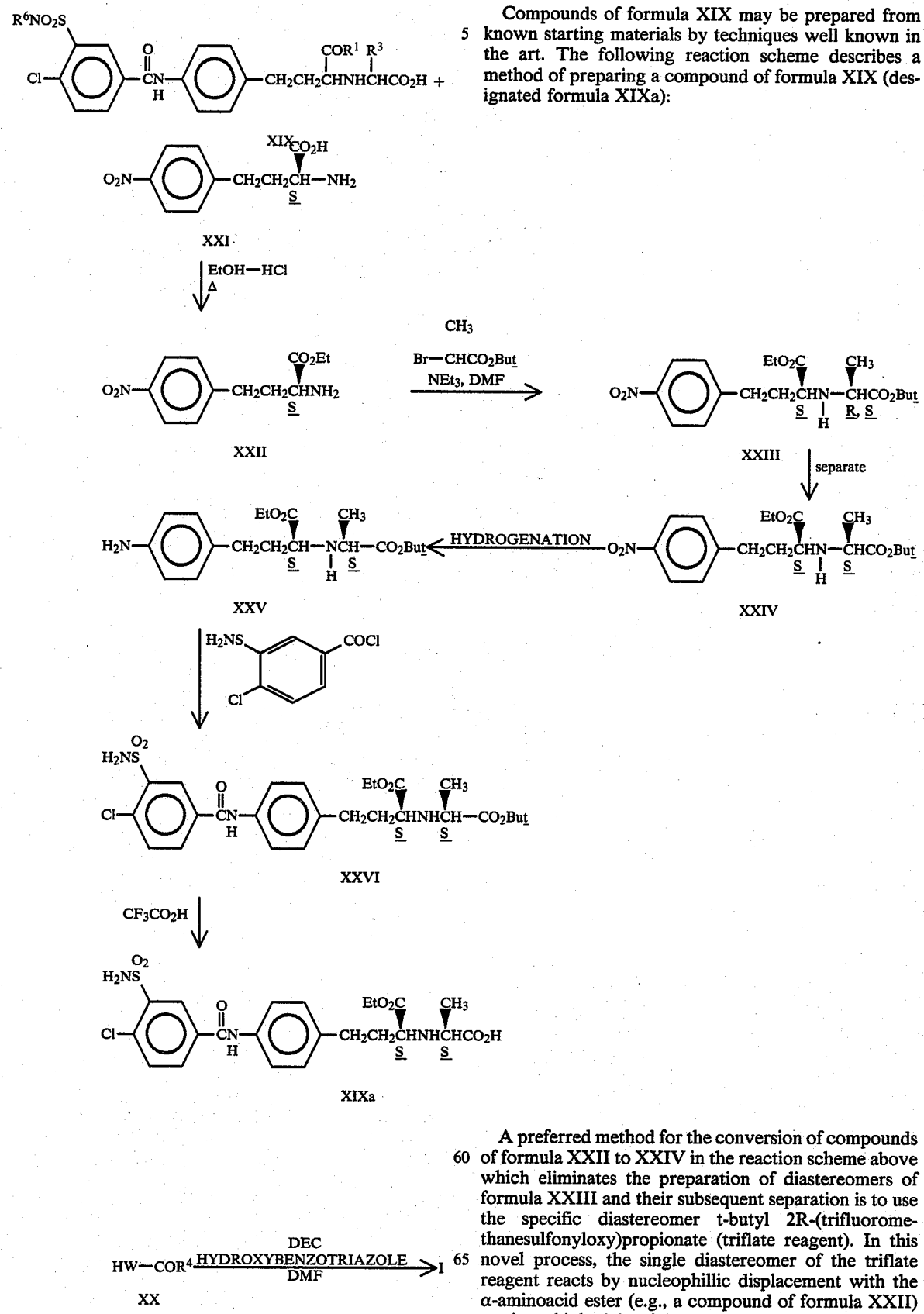

wherein $R^1$, $R^3$, $R^4$, $R^6$ and W are as defined above, and "DEC" refers to 1-(3-dimethylaminopropyl)-3-ethyl carbodiimide HCl.

Compounds of formula XIX may be prepared from known starting materials by techniques well known in the art. The following reaction scheme describes a method of preparing a compound of formula XIX (designated formula XIXa):

A preferred method for the conversion of compounds of formula XXII to XXIV in the reaction scheme above which eliminates the preparation of diastereomers of formula XXIII and their subsequent separation is to use the specific diastereomer t-butyl 2R-(trifluoromethanesulfonyloxy)propionate (triflate reagent). In this novel process, the single diastereomer of the triflate reagent reacts by nucleophillic displacement with the α-aminoacid ester (e.g., a compound of formula XXII) to give a high yield of the corresponding specific single diastereomer of the resulting monoamino dicarboxylic acid ester (e.g., a compound of formula XXIV).

Since the preferred compounds of formula I have an S-configuration at the carbon to which $R^3$ is attached the triflate reagent used herein is the 2-R diastereomer (see Preparation 4). However, the process is generally applicable to converting a broad range of α-aminoacid esters to the desired specific single diastereomer by using the appropriate triflate diastereomer. In place of the t-butyl ester of the triflate, other lower alkyl esters or the benzyl ester may be used.

The reaction proceeds at room temperature (i.e., 20°–50° C., preferably about 25° C.) in an inert solvent such as chloroform, dichloromethane, carbontetrachloride, benzene, toluene, or ethyl acetate in the presence of a base such as a tertiary amine (e.g., triethylamine or N-methylmorpholine). The reaction is complete in about 24 hours or less. The desired compound is recovered from the reaction mixture and purified by standard techniques. For example, the crude product is extracted into an organic solvent such as ether and concentrated to a crude oil, which is then purified by column chromatography to yield the desired specific diastereomer.

Carboxy-protected compounds of formula XX are prepared by methods well known in the art. See, for example, Neustadt et al. in European Patent Application No. 50,800, published May 5, 1982.

Alternatively, compounds of formula I wherein Y is —$CH_2$—, and Z is a group of formula VII may be prepared by the reaction of an acid chloride of formula XXVII with a dipeptide of formula XXVIII:

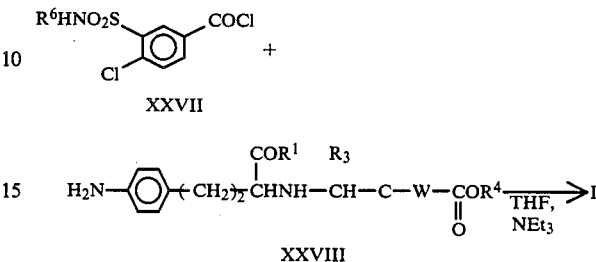

wherein $R^1$, $R^3$, $R^4$, $R^6$ and W are as defined above.

Compounds of formula XXVII may be prepared by known methods.

Compounds of formula XXVIII may be prepared by well known methods, an example of which is shown in the following reaction scheme:

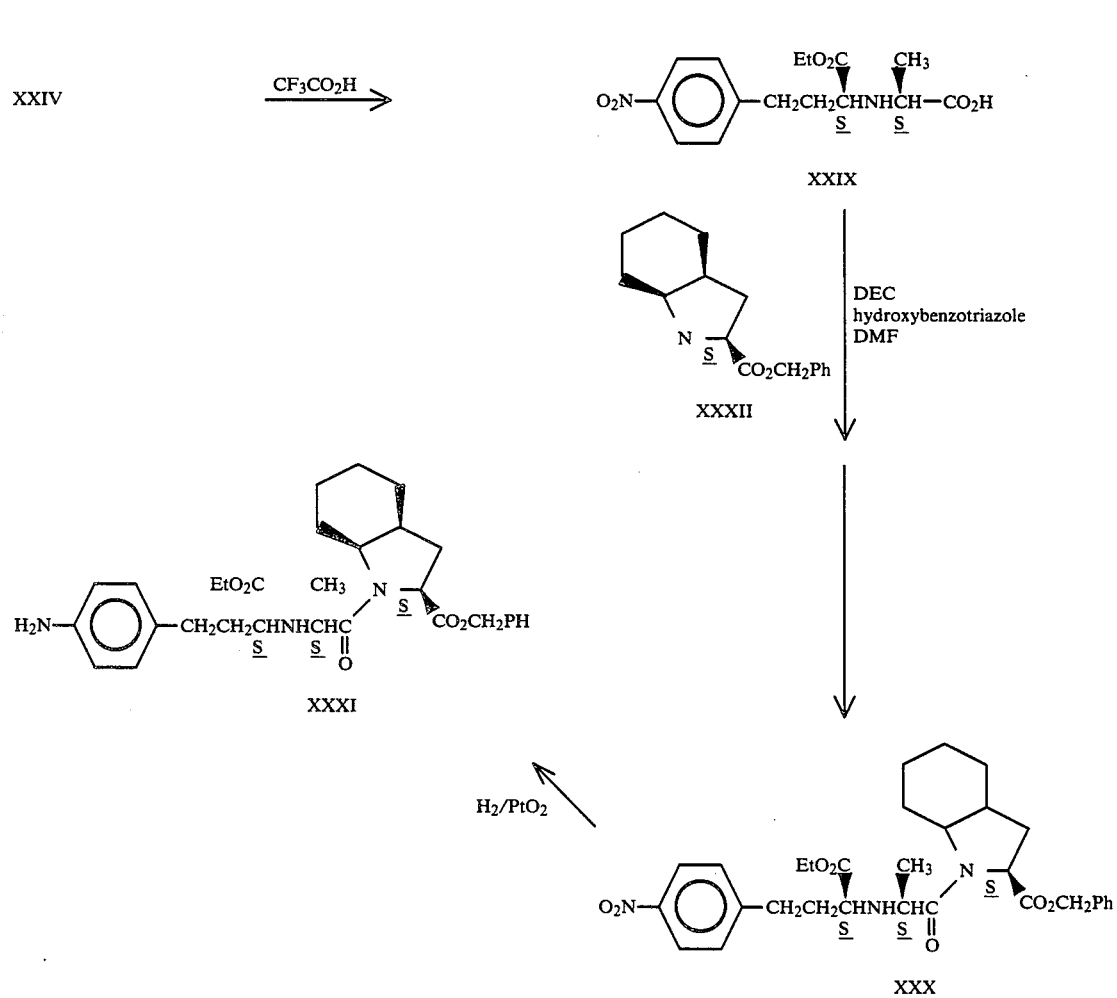

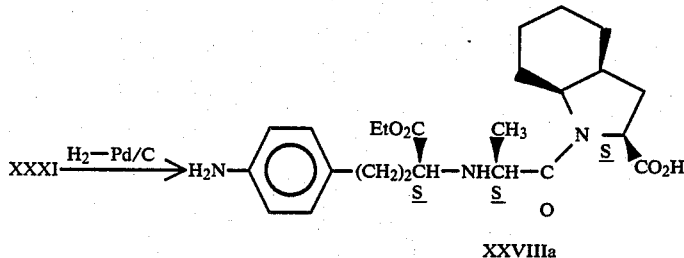

XXVIIIa

Alternatively, XXX may be hydrogenated directly to give XXVIIIa using a catalyst such as palladium on carbon.

Alternatively, XXXII may be reacted with a compound of formula XIXa to give a compound of formula I wherein $R^4$ is benzyloxy. The benzyloxy group may be then removed by hydrogenation with an appropriate catalyst such as palladium on carbon.

The known coupling methods above include amino group protection during the coupling reaction, for example by N-formyl, N-t-butoxycarbonyl and N-carbobenzyloxy groups, followed by their removal to yield compounds of formula I. Furthermore, the $COR^4$ function wherein $R^4$ is OH may be protected by removable ester groups such as benzyl, ethyl, t-butyl and the like.

The more complex esters at $R^1$ (i.e., $R^1$ is other than hydroxy or alkoxy) are most conveniently prepared by esterifying compounds of formula I wherein $R^1$ is hydroxy and $R^4$ is benzyloxy with the appropriate reagent, then removing the benzyl ester at $R^4$. For example, compounds of formula I where $R^1$ is hydroxy and $R^4$ is benzyloxy may be reacted with chloromethyl pivalate to obtain the corresponding pivaloyloxymethyl ester.

The following examples further illustrate the preparation of compounds of this invention.

PREPARATION 1

1-Pyruvoyl-cis,syn-Octahydro-1H-Indole-2(S)-Carboxylic Acid

A. Dissolve 27.0 g of ethyl indole-2-carboxylate in 250 ml of trifluoroacetic acid. Add 2.05 g of platinium oxide, hydrogenate the mixture at 50 lb/in$^2$ at room temperature. Filter the mixture and concentrate the filtrate in vacuo to give a residue. Suspend the residue in ether and treat with cold dilute sodium hydroxide solution. Dry the organic layer over magnesium sulfate and concentrate it to give ethyl octahydroindole-2-carboxylate, a pale yellow oil.

B. Dissolve 116 g of 10-d-camphorsulfonic acid in 1 liter of warm ethyl acetate and add a solution of 86 g of the product of part A in 1 liter of ethyl acetate. Allow the mixture to crystallize, heat to reflux, cool to room temperature, and filter. Recrystallize the filter cake from a mixture of 500 ml of isopropanol and 1800 ml ethyl acetate, filter and dry the crystals to obtain 2(S)-carboethoxy-cis,syn-octahydro-1H-indole, d-10-camphorsulfonate, m.p. 192°–193° C.

C. Slurry 10 g of the product of part B in 1 liter of ether, adjust to pH 11 with aqueous sodium hydroxide, and stir for 5 minutes. Wash the organic layer with sodium chloride solution, dry over magnesium sulfate, filter, and evaporate in vacuo at room temperature to obtain 2(S)-carboethoxy-cis,syn-octahydro-1H-indole as a colorless oil. Dissolve the resultant oil in 50 ml of methanol containing 23 ml of 1N sodium hydroxide, stir at 25° C. for 30 minutes, adjust to pH 7 with 1N hydrochloric acid, and evaporate the solvent to give cis,syn-octahydro-1H-indole-2(S)-carboxylic acid.

D. Cool 23 ml of benzyl alcohol to 0° C. under nitrogen and add 5.95 g of thionyl chloride dropwise over 15 minutes, maintaining the temperature at 0° C. Add the product of part C, stir for 1 hour at 0° C., then stir for 24 hours at room temperature. Pour the resulting mixture into 500 ml of ether, stir 1 hour under nitrogen, then allow to stand under nitrogen until the solution is clear. Decant the supernatant, wash the precipitate with 25 ml of ether, then slurry the precipitate in 200 ml of ether and adjust to pH 8–9 with 1-N sodium hydroxide. Stir 5 minutes, wash the organic layer with sodium chloride solution, dry over magnesium sulfate, filter and evaporate in vacuo at room temperature to obtain cis,-syn-octahydroindole-2(S)-carboxylic acid, benzyl ester as a colorless oil (TLC in ether: one spot, Rf 0.3).

E. To 26 g of the product of part D in 100 ml of dichloromethane and 7.8 ml of pyridine add 11.0 g of pyruvoyl chloride and stir the resulting mixture at room temperature. Extract the reaction mixture with water and dry the organic layer over magnesium sulfate. Concentrate the dichloromethane solution in vacuo and distill the residue to give 1-pyruvoyl-cis,syn-octahydro-1H-indole-2(S)-carboxylic acid, benzyl ester.

F. To 20 g of the product from part E in 400 ml of ethanol, added 2.0 g of 10% palladium-on-charcoal and hydrogenate at 50 psi at room temperature. Filter the resulting mixture and concentrate the filtrate in vacuo to give the title compound.

PREPARATION 2

1-{N-[1(S)-Ethoxycarbonyl-2-(4-aminophenyl)ethyl]-(S)-alanyl}-cis,syn-octahydro-1H-indole-2(S)-carboxylic acid Method I A. To a solution of 4-nitrophenylalanine, ethyl ester, hydrochloride (54.0 g) in dry dimethylformamide (400 ml), add t-butyl 2-bromopropionate (112.3 g) and triethylamine (76 ml) and heat the resulting mixture at 70° for 18 hours under a nitrogen atmosphere. Pour the reaction mixture into water and extract with methylene chloride (6×300 ml). Combine the organic layers, dry over magnesium sulfate and concentrate in vacuo to give a liquid (contains DMF). Chromatograph this liquid on a Prep 500 (3 silica gel cartridges) using hexane (8 l) then hexane:ethylacetate 4:1 and isolate N-[1(S)-ethoxycarbonyl-2-(4-nitrophenyl)ethyl]-(R)alanine, t-butyl ester, $[\alpha]_D^{26} = +24.7°$ (methanol), and N-1(S)-ethoxycarbonyl-2-(4-nitrophenyl)ethyl]-(S)alanine, t-butyl ester.

B. Add cold trifluoroacetic acid (600 ml) (ice bath) to N-[1(S)-ethoxycarbonyl-2-(4-nitrophenyl)ethyl]-(S)- alanine, t-butyl ester (25.5 g) and stir the resulting mixture at room temperature under a nitrogen atmosphere for 4 hours. Concentrate the solution in vacuo to give a viscous oil. Triturate the viscous oil with hexane (3 l) and then ether to yield N-[1(S)-ethoxycarbonyl-2-(4-nitrophenyl)ethyl]-(S)-alanine.

C. To a solution of the product of Step B (17.84 g), cis,syn-octahydro-1H-indole-2(S)-carboxylic acid, benzyl ester (11.50 g), and triethylamine (4.46 g) in dimethylformamide (450 ml) at 0°–5° under a nitrogen atmosphere, add 1-hydroxybenzotriazole (6.76 g) and 1-(3-dimethylaminopropyl)-3-ethylcarbodiimide, hydrochloride (16.13 g). Stir the reaction mixture at 0°–5° for 25 minutes and then at room temperature for 90 minutes. Concentrate the reaction mixture in vacuo and partition between dichloromethane and saturated sodium bicarbonate solution. Dry the organic layer over magnesium sulfate and concentrate in vacuo to give a viscous oil which contains 1-{N-[1(S)-ethoxycarbonyl-2-(4-nitrophenyl)ethyl]-(S)-alanyl}-cis,syn-octahydro-1H-indole-2(S)-carboxylic acid, benzyl ester.

D. Hydrogenate the product from Step C above in absolute ethanol (250 ml) in the presence of 10% palladium on carbon at 60 psi in a Parr Shaker Apparatus. Remove the catalyst by filtration through celite and concentrate the filtrate in vacuo to give a foam. Chromatograph the foam on the Prep 500 (3 cartridges) using chloroform:methanol:ammonium hydroxide 200:30:5 as eluant to give the title compound $[\alpha]_D^{26} = -44.0°$ (MeOH).

Method II

A. To a solution of 4-nitrophenylalanine, ethylester, hydrochloride (2.3 g) in dichloromethane (10 ml), add triethylamine (2.55 ml) and then t-butyl 2(R)-(trifluoromethanesulfonyloxy)propionate (2.80 g) (see Preparation 4) in dichloromethane (10 ml). Stir the resulting solution at room temperature for 20 hours. Concentrate the reaction mixture, add diethyl ether and extract with salt solution. Dry over magnesium sulfate and concentrate the ether solution in vacuo to give an oil. Place the oil on a column of silica gel (100 ml, 60–200 mesh) and elute with diethyl ether:hexane 60:40 to give N-[1(S)-ethoxycarbonyl-2-(4-nitrophenyl)ethyl]-(S)-alanine, t-butyl ester.

B. to D. Proceed as described in Method I.

PREPARATION 3

1-{N[1(S)-Ethoxycarbonyl-3-(4-aminophenyl)propyl]-(S)-alanyl}-cis,syn-octahydro-1H-indole-2(S)-carboxylic acid Method I A. To a solution of 2-acetamido-4-(4-nitrophenyl)-butyric acid (57.65 g) in hot 95% ethanol (1000 ml) add d-(+)-α-methylbenzylamine (25.2 g) in hot 95% ethanol (125 ml), cool the solution slowly and keep at room temperature 18 hours. Collect the solid and wash with cold 95% ethanol, and dry to give an orange-yellow solid. Recrystallize this solid from 95% ethanol treated with charcoal to give 2(S)-acetamido-4-(4-nitrophenyl)-butyric acid, d-(+)-α-methylbenzyl amine salt $[\alpha]_D^{26} = +45.6$ (MeOH), m.p. 211°–213° C.

B. Suspend the product of part A (29.00 g) in ether (500 ml) and add 1N NaOH (150 ml). Separate the aqueous solution and wash with ether. Cool the aqueous solution in an ice-NaCl bath, add concentrated hydrochloric acid to pH 1 and stir the resulting mixture for 1 hour. Remove 2(S)-acetamido-4-(4-nitrophenyl)butyric acid, a white solid, $[\alpha]_D^{26} = +33.9°$ (MeOH), m.p. 266° C.

C. Treat the compound prepared in part B above (18.65 g) with 6N hydrochloric acid (700 ml) and heat the resulting mixture under reflux for 2.5 hours. Concentrate the solution in vacuo to give 2(S)-amino-4-(4-nitrophenyl)butyric acid, hydrochloride, a solid, m.p. 186°–189° C., $[\alpha]_D^{26} = +46.9°$ (MeOH).

D. Heat the compound prepared in part C (19.30 g) in absolute ethanol saturated with hydrogen chloride acid (400 ml) under reflux for 1½ hour. Remove the solvent in vacuo and triturate the residue with ether to give 2(S)-amino-4-(4-nitrophenyl)butyric acid, ethyl ester, hydrochloride, a white solid m.p. 288.5° $[\alpha]_D^{26} + 40.6°$ (MeOH).

E. Treat the compound prepared in part D (18.00 g) in dry dimethylformamide (250 ml) with t-butyl 2-bromopropionate (35.20 g) and trimethylamine (18.90 g) as described in Preparation 2A. Use Prep 500 (2 cartridges) and hexane (6 l) and then hexane/ethyl acetate 8:1 as eluants and isolate N-[1(S)-ethoxycarbonyl-3-(4-nitrophenyl)propyl]-(S)-alanine, t-butyl ester $[\alpha]_D^{26} = -8.0°$ (MeOH).

F. To the product of part E (6.90 g) at 0°, add trifluoroacetic acid (500 g) and treat the resulting mixture as described in Preparation 2B and isolate N-[1(S)-ethoxycarbonyl-3-(4-nitrophenyl)propyl]-(S)-alanine, trifluoroacetic acid salt, a viscous oil.

G. To a cold (0°–5°) solution of the product of part F (6.68 g) and cis,syn-octahydro-1H-indole-2(S)-carboxylic acid, benzyl ester (3.95 g) in anhydrous dimethylformamide (250 ml) and triethylamine (3.38 g), add 1-hydroxybenzotriazole (2.80 g) and 1-(3-dimethylaminopropyl)-3-ethylcarbodiimide, hydrochloride (5.85 g) and stir the resulting mixture at 0°–5° C. for 30 minutes and then at room temperature for 1.5 hour. Pour the reaction mixture into saturated sodium bicarbonate and extract with dichloromethane (2×1 l). Dry the organic layer over magnesium sulfate and concentrate in vacuo to give a viscous oil. Chromatograph this oil on the Prep 500 (2 cartridges) using ethyl acetate:hexane 3:20 and then 1:1 and isolate 1-{N[1(S)-ethoxycarbonyl-3-(4-nitrophenyl)propyl]-(S)-alanyl}-cis,syn-octahydro-1H-indole-2(S)-carboxylic acid, benzyl ester.

H. Hydrogenate the product of part G (4.69 g) in absolute ethanol (250 ml) in the presence of 5% palladium-on-charcoal (0.50 g) at 60 psi in a Parr Shaker Apparatus. Remove catalyst by filtration and concentrate the filtrate to give the title compound, a foam $[\alpha]_D^{26} = -29.7°$ (MeOH).

Method II

A. to D. Proceed as described in Method I.

E. Treat the product of part D as described in Preparation 2, Method II, part A to obtain N-[1(S)-ethoxycarbonyl)-3-(4-nitrophenyl)propyl]-(S)-alanine, t-butyl ester.

F. to H. Proceed as described in Method I.

PREPARATION 4 t-Butyl 2R-(Trifluoromethanesulfonyloxy)Propionate

A. Add 2S-(p-toluenesulfonyloxy)propionic acid (4.4 g) to a cold solution of 10 ml isobutylene and 0.4 ml concentrated sulfuric acid in 30 ml methylene chloride in a pressure vessel, seal, and agitate at room temperature for 48 hours. Pour into 50 ml 15% sodium carbonate solution, dry over magnesium sulfate and concentrate to obtain t-butyl 2S-(p-toluenesulfonyloxy)propionate as an oil (NMR 1.37). Distilled material (Kugelrohr, 120°) has $[\alpha]_D^{26} = -45.9°$ (EtOH, c=1).

B. Combine the product of part A (100 g) with acetic acid (40.0 g) and triethylamine (67.2 g) in 200 ml dry DMF. Heat at 65° for 20 hours. Partition with 2 l each ether and water, and wash the ether with citric acid, then with sodium bicarbonate solution. Dry and concentrate the ether solution to obtain t-butyl 2R-acetoxypropionate as a colorless liquid, bp 50° C./0.1 mm.

C. Combine the product of part B (62.6 g) with ethylenediamine (11.6 g) and heat at 70° for 24 hours. Allow to cool, add 300 ml ether and filter. Wash the ether with water, 10% citric acid, and then in sodium bicarbonate solution. Dry and concentrate the ether solution to leave a colorless oil. Crystallize from hexane at −20° to give t-butyl 2R-hydroxypropionate as white needles, m.p. 41°-2° C.

D. Combine the product of part C (7.3 g) with pyridine (4.0 g) in 50 ml methylene chloride. Cool to −5° C., and add dropwise a solution of trifluoromethanesulfonic anhydride (14.1 g) in 25 ml methylene chloride. Allow the reaction to reach room temperature, then wash successively with water, 1N sulfuric acid and 1N sodium bicarbonate solution. Dry and concentrate the methylene chloride solution to leave the title compound as a colorless oil.

NMR (in CDCl3)=5.10 q; 1.73 d; 1.50 s.

EXAMPLE 1

1-{N-[1(S)-Ethoxycarbonyl-2-[4-(3-sulfamoyl-4-chlorobenzamido)phenyl]ethyl]-(S)-alanyl}-cis,syn-octahydro-1H-indole-2(S)-carboxylic acid To a 0°-5° C. solution of the product of Preparation 2 (2.00 g) in anhydrous tetrahydrofuran (100 ml) and triethylamine (0.94 g), add a solution of 4-chloro-3-sulfamoylbenzoylchloride (1.61 g) in anhydrous tetrahydrofuran (10 ml) over a period of 30 minutes. Stir the resulting mixture for 15 minutes at 0°-5° and then at room temperature for 18 hours. Filter the reaction mixture and concentrate the filtrate in vacuo to give a residue. Chromatograph the residue on the Prep 500 (1 cartridge) using chloroform:methanol:ammonium hydroxide 200:30:5 as eluant to give the title compound, a foam, $[\alpha]_D^{26} = -16.1°$ (MeOH).

In a similar manner, using appropriate starting materials, prepare the following:

1-{N-[1(S)-ethoxycarbonyl-2-[4-(4-chloro-3-N-methylsulfamoylbenzamido)phenyl]ethyl]-(S)-alanyl}-cis,-syn-octahydro-1H-indole-2(S)-carboxylic acid, $[\alpha]_D^{26} = -18.7°$ (methanol).

1-{N-[1(S)-ethoxycarbonyl-3-[4-(2-hydroxy-4-chloro-5-sulfamoylbenzamido)phenyl]ethyl]-(S)-alanyl}-cis,-syn-octahydro-1H-indole-2(S)-carboxylic acid, $[\alpha]_D^{26} = -18.1°$ (methanol).

EXAMPLE 2

1-{N-[1(S)-Carboxy-2-[4-(4-chloro-3-sulfamoylbenzamido)phenyl]ethyl]-(S)-alanyl}-cis,syn-octahydro-1H-indole-2(S)-carboxylic acid To the product of Example 1 (0.35 g) add 0.5N NaOH (5 ml) and stir at room temperature for 1 hour. Add Bio-Rad Resin (AG 50W-X3, 100-200 mesh, hydrogen form) and then add to a column of the same resin. Elute with water (200 ml) and then water:pyridine 96:4. Concentrate the desired fractions to give the title compound. $[\alpha]_D^{26} = -7.0°$ (MeOH).

In a similar manner, prepare 1-{N[1(S)-carboxyl-2-[4-(4-chloro-3-N-methylsulfamoylbenzamido)phenyl]ethyl]-(S)-alanyl}-cis,syn-octahydro-1H-indole-2(S)-carboxylic acid, $[\alpha]_D^{26} = 8.9°$ (methanol).

EXAMPLE 3

1-{N-[1(S)-Ethoxycarbonyl-3-[4-(4-chloro-3-sulfamoylbenzamido)phenyl]propyl]-(S)-alanyl}-cis,syn-octahydro-1H-indole-2(S)-carboxylic acid To a 0°-5° solution of the compound of Preparation 3 (1.50 g) in anhydrous tetrahydrofuran (100 ml) and triethylamine (0.68 g), add a solution of 4-chloro-3-sulfamoylbenzoylchloride (1.11 g) and treat as described in Example 1, except use chloroform (2 l) and then chloroform:methanol:ammonium hydroxide 100:30:5 as eluants and isolate the title compound, a foam $[\alpha]_D^{26} = -9.1$ (methanol).

In a similar manner using appropriate starting materials, prepare 1-{N-[1(S)-Ethoxycarbonyl-3-[4-(4-chloro-3-N-methylsulfamoylbenzamido)phenyl]propyl]-(S)-alanyl}cis,syn-octahydro-1H-indole-2(S)-carboxylic acid.

EXAMPLE 4

1-{N-[1(S)-Carboxy-2-([4-[(6-Chloro-3,4-Dihydro-7-Sulfamyl-2H-1,2,4-Benzothiadiazin-3-yl-1,1-Dioxide)-Methyloxy]Phenyl]Methylthioethyl)-(S)-Alanyl}-cis,-syn-Octahydro-1H-Indole-2(S)-Carboxylic Acid A. Combine bromoacetaldehyde diethylacetal (19.7 g) and p-cresol (10.8 g) in dry dimethylformamide (DMF) (100 ml) and stir. Add potassium t-butoxide (9.6 g) and continue stirring for 24 hours, then evaporate the DMF in vacuo. Partition the resultant residue between ethyl acetate and water. Separate the organic layer, wash with 10% aqueous sodium hydroxide followed by brine, then dry the organic layer over sodium sulfate and filter. Evaporate the solvent in vacuo and purify the crude product on a silica gel column to obtain 4-[2,2-diethoxy)ethoxy]toluene:

NMR δ=1.12 (6H, t,CH3); 2.15 (s, 3H,—CH3); 3.55 (q 4H, CH2—O); 3.90(d, 2H, CH2-phenyl); 4.77 (t,1H, —CH2—); and 6.80 (m, 4H, Ar).

B. Combine N-bromosuccinamide (0.877 g) and the product of Step A (1 g) in carbon tetrachloride (20 ml) and stir at reflux for 18 hours. Filter the resultant solid and evaporate the solvent in vacuo to obtain 4-[(2,2-diethoxy)ethoxy]benzyl bromide:

NMR=1.10 (t, 6H, CH); 3.59 (q, 4H, —OCH2); 3.86 (d, 2H, C—CH2O); 4.31(s, 2H, CH2—Br); 4.70 (t, 1H, —CH—); 7.00 (m, 4H, Ar).

C. Combine methyl alcohol (20 ml) and 19M sodium hydroxide (10 ml). Add L-cysteine (0.1 g), stir for 15 minutes, then add the product of Step B and stir at room temperature overnight. Adjust the resultant solution to approx. pH 7 and filter the resultant solid. Wash the solid with ether and dry under vacuum to obtain (S)-4-[(2,2-diethoxy)ethoxybenzyl]cysteine.

D. Dissolve 4-amino-6-chloro-1,3-benzenedisulfonamide (0.74 g) in dimethoxyethane (10 ml), add the product of Step C (0.99 g), stir while heating to reflux, and add 2 drops of concentrated hydrochloric acid. Reflux 4 hours, then evaporate the solvent in vacuo. Wash the resultant solid with ether and dry under vacuum to obtain S-[4-[(6-chloro-3,4-dihydro-7-sulfamyl-2H-1,2,4-benzothiadiazin-3-yl-1,1-dioxide)methoxy]benzyl-L-cysteine.

E. React 0.02 moles of the product of part D in 20 ml of tetrahydrofuran with 0.02 moles of the product of Preparation 1 and add 20 ml of molecular sieves 4 A (Rohm and Haas). Stir the resulting mixture for 4 hours, add 12 g of sodium cyanoborohydride in 20 ml of methanol and stir the reaction mixture 20 hours. Filter, concentrate to dryness, and partition the residue between water and dichloromethane. Absorb the aqueous phase on strong acidic ion-exchange resin and elute with 4% pyridine in water. Separate the isomers on a column of silica gel using CHCl$_3$:isopropanol:7% ammonium hydroxide 1:1:1 (organic phase) as eluant to give the title compound.

EXAMPLE 5

1-{N-[1(S)-Ethoxycarbonyl-2-[4-(6-chloro-3,4-dihydro-1,1-dioxo-7-sulfamoyl-1,2,4-benzothiadiazine-3-acetamido)phenyl]ethyl]-(S)-alanyl}-cis,syn-octahydro-1H-indole-2(S)-carboxylic acid A. Hydrogenate a solution of N-[1(S)-ethoxycarbonyl-2-(4-nitrophenyl)ethyl]-(S)-alanine, t-butyl ester (20.0 g) (see Preparation 2, IA) in absolute ethanol (500 ml) in the presence of 10% palladium on carbon (1.5 g) at 50 psi in a Parr shaker apparatus. Remove the catalyst by filtration and concentrate the filtrate in vacuo to give N-[1(S)-ethoxycarbonyl-2-(4-aminophenyl)ethyl]-(S)-alanine, t-butyl ester.

B. To a solution of the product of part A in dimethylformamide (150 ml), add 6-chloro-3,4-dihydro-1,1-dioxo-7-sulfamoyl-1,2,4-benzothiadiazine-3-acetic acid (14.4 g), 1-hydroxybenzotriazole (6.8 g) and 1-(3-dimethylaminopropyl)-3-ethylcarbodiimide, hydrochloride (9.6 g) at 0°–5°. Warm the reaction mixture to room temperature and stir for 18 hours. Concentrate the reaction mixture in vacuo, add dichloromethane and concentrate in vacuo. Dissolve the residue in ethyl acetate and extract with 1N sodium bicarbonate. Dry (MgSO$_4$) and concentrate the ethyl acetate solution in vacuo. Chromatograph the residue on silica gel using the Water Prep 500 using ethylacetate as eluant to give N-[1(S)-ethoxycarbonyl-2-[4-(6-chloro-3,4-dihydro-1,1-dioxo-7-sulfamoyl-1,2,4-benzothiadiazine-3-acetamido)phenyl]ethyl]-(S)-alanine, t-butyl ester.

C. Treat the product (11.0 g) prepared in Example 5B with dioxane saturated with hydrogen chloride (100 ml) for 20 hours at RT. Concentrate the reaction mixture in vacuo and tritrate the residue with anhydrous ether to isolate N-[1(S)-ethoxycarbonyl-2-[4-(6-chloro-3,4-dihydro-1,1-dioxo-7-sulfamoyl-1,2,4-benzothiadiazine-3-acetamido)phenyl]ethyl-(S)-alanine hydrochloride salt.

D. Treat the product of part C as described in Preparation 2I, C to obtain {1-N-[1(S)-[ethoxycarbonyl-2-[4-(6-chloro-3,4-dihydro-1,1-dioxo-7-sulfamoyl-1,2,4-benzothiadiazine-3-acetamido)phenyl]ethyl]-(S)-alanyl}-cis,syn-octahydro-1H-indole-2(S)-carboxylic acid, benzyl ester.

E. Treat the product (7.3 g) of part D with 20% HBr in glacial acetic acid (30 ml) at 0°–5° and then stir at room temperature for 3 hr. Concentrate the reaction mixture in vacuo and wash the residue with ether to give the title compound, hydrobromide.

F. Treat the product (3.0 g) of part E with Bio-Rad Resin (AG 50W-X2, 100–200 mesh) in water and then add to a column of the same resin. Elute with water, then water:pyridine 96:4 and then water:pyridine:absolute ethanol 76:20:4. Concentrate the fractions (iodine positive) in vacuo to give the title compound.

EXAMPLE 6

1-{N-[1(S)-Carboxy-2-[4-(6-chloro-3,4-dihydro-1,1-dioxo-7-sulfamoyl-1,2,4-benzothiadiazine-3-acetamido)phenyl]ethyl]-(S)-alanyl}cis,syn-octahydro-1H-indole-2(S)-carboxylic acid To the product from Example 5 (3.0 g) add 1N NaOH (20 ml) and treat as described in Example 2 to give the title compound.

EXAMPLE 7

1-{N-[1(S)-Ethoxycarbonyl-3-[4-(6-chloro-3,4-dihydro-1,1-dioxo-7-sulfamoyl-1,2,4-benzothiadiazine-3-acetamido)phenyl]propyl]-(S)-alanyl}-cis,syn-octahydro-1H-indole-2(S)-carboxylic acid Treat the product of Preparation 3IE as described in Example 5 to produce the title compound.

EXAMPLE 8

1-{N-[1(S)-Carboxy-3-[4-(6-chloro-3,4-dihydro-1,1-dioxo-7-sulfamoyl-1,2,4-benzothiadiazine-3-acetamido)phenyl]propyl]-(S)-alanyl}cis,syn-octahydro-1H-indole-2(S)-carboxylic acid Treat the product of Example 7 as described in Example 2 to produce the title compound.

By following the procedures described in the above preparations and examples, and by using the appropriate reagents, the following compounds may be prepared:

1-{Nα-[1(S)-ethoxycarbonyl-3-[4-(6-chloro-3,4-dihydro-1,1-dioxo-7-sulfamoyl-1,2,4-benzothiadiazine-3-acetamido)phenyl]propyl]-(S)-lysyl}-cis,syn-octahydro-1H-indole-2(S)-carboxylic acid;

1-{N-[1(S)-methoxycarbonyl-4-[4-(6-chloro-3,4-dihydro-1,1-dioxo-7-sulfamoyl-1,2,4-benzothiadiazine-3-acetamido)phenyl]butyl]-(S)-alanyl}-cis,syn-octahydro-1H-indole-2(S)-carboxylic acid;

2-{N-[1(S)-ethoxycarbonyl-3-[4-(6-chloro-3,4-dihydro-1,1-dioxo-7-sulfamoyl-1,2,4-benzothiadiazine-3-acetamido)phenyl]propyl]-(S)-alanyl}-1,2,3,4-tetrahydroisoquinoline-3(S)-carboxlic acid;

1-{N-[1(S)-(2-phenoxyethoxycarbonyl)-3-[4-(4-chloro-3-sulfamoylbenzamido)phenyl]propyl]-(S)-alanyl}-cis,syn-octahydro-1H-indole-2(S)-carboxylic acid;

1-{N-[1(S)-pivaloyloxymethoxycarbonyl)-3-[4-(4-chloro-3-sulfamoylbenzenesulfonamido)phenyl]propyl]-(S)-alanyl}-cis,syn-octahydro-1H-indole-2(S)-carboxylic acid;

1-{N-[1(S)-ethoxycarbonyl-3-[4-(6-chloro-3,4-dihydro-1,1-dioxo-2-methyl-7-methylsulfamoyl-1,2,4-benzothiadiazine-3-acetamido)phenyl]propyl]-(S)-alanyl}-cis,syn-octahydro-1H-indole-2(S)-carboxylic acid;

1-{N-[1(S)-ethoxycarbonyl-3-[4-(4-chloro-3-sulfamoylbenzenesulfonamido)phenyl]propyl]-(S)-alanyl}-(S)-proline;

1-{N-[1(S)-carboxy-3-[4-(6-chloro-3,4-dihydro-1,1-dioxo-7-sulfamoyl-1,2,4-benzothiadiazine-3-acetamido)phenyl]propyl]-(S)-alanyl}-(S)-proline;

7-{N-[1(S)-carboxy-3-[4-(6-chloro-3,4-dihydro-1,1-dioxo-7-sulfamoyl-1,2,4-benzothiadiazine-3-acetamido)phenyl]propyl]-(S)-alanyl}-1,4-dithia-7-azaspiro[4.4]nonane-8(S)-carboxylic acid;

7-{N-[1(S)-carboxy-3-[4-(4-chloro-3-sulfamoylbenzamido)phenyl]propyl]-(S)-alanyl}-1,4-dithia-7-azaspira[4.4]nonane-8(S)-carboxylic acid;

2-{N-[1(S)-carboxy-3-[4-(4-chloro-3-sulfamoylbenzenesulfonamido)phenyl]propyl]-(S)-alanyl}-1,2,3,4-tetrahydroisoquinoline-3(S)-carboxylic acid;

1-{N-[1(S)-ethoxycarbonyl-4-[2-(6-trifluoromethyl-3,4-dihydro-1,1-dioxo-7-sulfamoyl-1,2,4-benzothiadiazinyl-3-acetamido)phenyl]propyl]-glycyl}-cis,syn-octahydro-1H-indole-2(S)-carboxylic acid;

1-{N-[1(S)-ethoxycarbonyl-2-[4-(6-chloro-3,4-dihydro-2-benzyl-1,1-dioxo-7-sulfamoyl-1,2,4-benzothiadiazine-3-acetamido)phenylthio]ethyl]-(S)-alanyl}-cis,-syn-octahydro-1H-indole-2(S)-carboxylic acid;

1-{N-[1(S)-ethoxycarbonyl-2-[4-(6-chloro-3,4-dihydro-1,1-dioxo-7-sulfamoyl-1,2,4-benzothiadiazine-2-benzyl-3-acetamido)phenyl]methoxyethyl]-(S)-alanyl}-cis,syn-octahydro-1H-indole-2(S)-carboxylic acid;

1-{N-[1(S)-ethoxycarbonyl-3-[4-(6-chloro-3,4-dihydro-1,1-dioxo-7-sulfamoyl-1,2,4-benzothiadiazin-3-yl)methylthiophenyl]propyl]-(S)-alanyl}-cis,syn-octahydro-1H-indole-2(S)-carboxylic acid;

The compounds of this invention are useful in view of their pharmacological properties. In particular, they possess activity as antihypertensive agents, as evidenced by their ability to reduce blood pressure in mammals in which the blood pressure has become abnormally elevated.

Since these compounds are believed to act as angiotensin converting enzyme inhibitors, it is also contemplated that they may be used in treating other cardiovascular disorders, for example congestive heart failure, and glaucoma in the same manner as other ACE inhibitors such as captopril and enalapril may be used.

The compounds of this invention can be combined with pharmaceutical carriers and administered in a variety of well-known pharmaceutical forms suitable for oral or parenteral administration to provide compositions useful in the treatment of cardiovascular disorders and particularly mammalian hypertension.

The effective daily antihypertensive dose (ED50) of the compounds of this invention will typically be in the range of about 0.1 to about 25 mg/kg, of mammalian weight, adminstered in single or divided doses. The exact dose to be administered in determined by the attending clinician and is dependent upon where the particular compound lies within the above quoted range, as well as upon the age, weight and condition of the individual.

Generally, in treating humans having hypertension, the compounds of this invention may be administered to patients in need of such treatment in a dosage range of about 5 to about 500 mg per patient generally given several times a day, thus giving a total daily dose of from about 5 to about 2000 mg per day.

The antihypertensive compositions containing the compounds of this invention will preferably contain from about 5 to about 250 mg of the active compound per dosage unit.

The compositions of the present invention are most preferably administered orally. Typical formulations for oral administration are those such as tablets, capsules, syrups, elixirs or suspensions. Typical injectable formulations include solutions and suspensions. Also contemplated are mechanical delivery systems, e.g. transdermal dosage forms.

The typical acceptable pharmaceutical carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; non-ionic, cationic and anionic sufactants; ethylene glycol polymers; betacyclodextrin; fatty alcohols and hydrolyzed cereal solids; as well as other non-toxic compatible filters, binders, disintegrants, buffers, preservatives, antioxidants, lubricants, flavoring agents, and the like commonly used in pharmaceutical formulations.

In the following examples, the "active ingredient" is 1-{N-[1(S)-ethoxycarbonyl-3-[4-(6-chloro-3,4-dihydro-1,1-dioxo-7-sulfamoyl-2H-1,2,4-benzothiadiazine)acetamido]phenyl]propyl]-(S)-alanyl}-cis,-syn-octahydro-1H-indole-2(S)-carboxylic acid. It is contemplated, however, that this compound may be replaced by equally effective quantities of other compounds within the scope of formula I.

EXAMPLE 10

| Capsule | Amount (mg) | |
|---|---|---|
| Active ingredient | 250.0 | 125.0 |
| Lactose | 173.0 | 86.5 |
| Corn Starch | 75.0 | 37.5 |
| Magnesium stearate | 2.0 | 1.0 |
| | 500.0 | 250.0 |

Blend the active ingredient, lactose, and corn starch until uniform; then blend the magnesium stearate into the resulting powder. Encapsulate the mixture into suitably sized two-piece hard gelatin capsules.

EXAMPLE 11

| Tablet | Amount (mg) | |
|---|---|---|
| Active Ingredient | 250.0 | 125.0 |
| Lactose | 161.0 | 80.5 |
| Corn Starch | 12.0 | 6.0 |
| Water (per thousand tablets) | 120 ml (evaporates) | 60 ml (evaporates) |
| Corn Starch | 75.0 | 37.5 |
| Magnesium Stearate | 2.0 | 1.0 |
| | 500.0 | 250.0 |

Blend the active ingredient with the lactose until uniform. Blend the smaller quantity of corn starch with the water and add the resulting corn starch paste, then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintegration.

EXAMPLE 12

| Injectable Solution | mg/ml |
|---|---|
| Active ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad. | 1.0 ml |

Dissolve the p-hydroxybenzoates in a portion of water for injection at 60°–70° C. and cool the solution to 25°–25° C. Charge and dissolve all other excipients and the active ingredient. Bring the solution to final volume, filter it through a sterilizing membrane and fill into sterile containers.

Similarly, substitute other compounds of the present invention to prepare other compositions of the present invention.

We claim:

1. A compound represented by the formula:

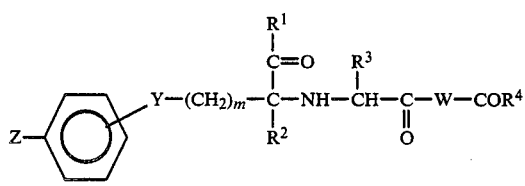

wherein
W is

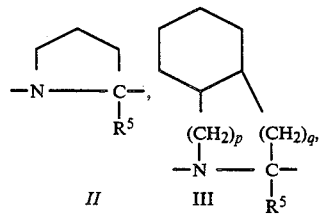

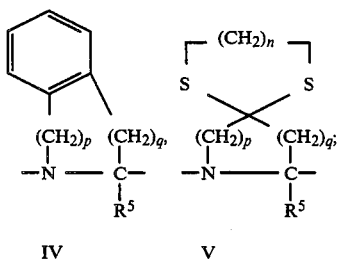

n is 0 or 1;
m is 0 to 2;
p and q are each 0, 1 or 2, provided that the sum of p and q is 1 or 2, and that in formula V, p is not 0;
Y is —CH$_2$—, —CH$_2$O—, or —CH$_2$S—, attached at the 2 or 4 position of phenyl group;
Z is

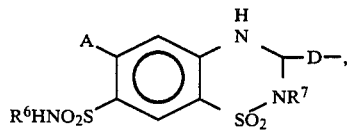

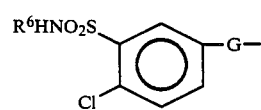

wherein
A is Cl or CF$_3$;
D is —(CH$_2$)$_u$—, —CH$_2$O—, —CH$_2$S—;

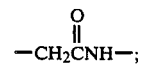

G is —CONR$^7$(CH$_2$)$_t$—, or —SO$_2$NR$^7$(CH$_2$)$_t$—;
t is 0 or 1;
R$^1$ and R$^4$ are independently hydroxy, alkoxy having from 1 to 8 carbon atoms, K—X$_r$—(CH$_2$)$_s$—O—, wherein K is phenyl, substituted phenyl, 1- or 2-naphthyl, X is oxygen or sulfur, r is 0 or 1 and s is 0 to 4, and wherein the substituents on the phenyl are chosen from group M, wherein M is halogen, hydroxy, trifluoromethyl, alkoxy having 1 to 6 carbon atoms, 2- and 3-furanyl, 2- and 3-thienyl and phenyl (which phenyl group may be substituted with halogen, hydroxy, trifluoromethyl, alkoxy having from 1 to 6 carbon atoms or alkyl having from 1 to 6 carbon atoms), provided that when s is zero, r is zero, —OCH$_2$OCO-alkyl wherein the alkyl has from 3 to 8 carbon atoms, —OCH$_2$CO-phenyl, wherein the phenyl may be substituted with group M, 1-glyceryl,

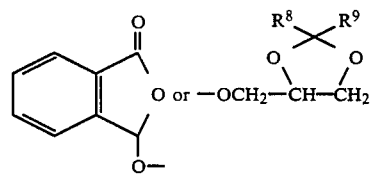

R$^2$, R$^5$, R$^6$ and R$^9$ are hydrogen or lower alkyl;
R$^3$ is hydrogen, lower alkyl or amino lower alkyl;
R$^7$ is hydrogen, lower alkyl or phenyl(lower)alkyl;
R$^8$ is hydrogen, lower alkyl, phenyl, or phenyl substituted by group M;
u is 1 or 2;
and the pharmaceutically acceptable salts thereof.

2. A compound of claim 1 wherein W is represented by formula III, IV or V.

3. A compound of claim 1 wherein W is represented by formula III or V.

4. A compound of claim 1 wherein W is represented by formula III or IV, wherein p is 0 and q is 1.

5. A compound of claim 1 wherein W is represented by formula V, wherein p is 1, q is 1, and n is 0.

6. A compound of claim 1 wherein R$^2$ and R$^5$ are hydrogen.

7. A compound of claim 1 wherein R$^4$ is hydroxy.

8. A compound of claim 4 wherein R$^3$ is methyl or aminobutyl.

9. A compound of claim 5 wherein $R^3$ is methyl or aminobutyl.

10. A compound of claim 8 wherein Z is represented by formula VI.

11. A compound of claim 9 wherein Z is represented by formula VI.

12. A compound of claim 10 wherein A is chlorine, and $R^6$ and $R^7$ are hydrogen or methyl.

13. A compound of claim 11 wherein A is chlorine, $R^6$ and $R^7$ are hydrogen or methyl.

14. A compound of claim 8 wherein Z is represented by formula VII.

15. A compound of claim 9 wherein Z is represented by formula VII.

16. A compound of claim 14 wherein $R^6$ is hydrogen or methyl.

17. A compound of claim 15 wherein $R^6$ is hydrogen or methyl.

18. A compound of claim 1 wherein $R^1$ is hydroxy, ethoxy, methoxy, phenoxyethoxy, or pivaloyloxymethoxy.

19. A compound of claim 1 which is 1-{N-[1(S)-ethoxycarbonyl-2-[4-(3-sulfamoyl-4-chlorobenzamido)-phenyl]ethyl]-(S)-alanyl}-cis,syn-octahydro-1H-indole-2(S)-carboxylic acid.

20. A compound of claim 1 which is 1-{N-[1(S)-ethoxycarbonyl-2-[4-(4-chloro-3-N-methylsulfamoylbenzamido)phenyl]ethyl]-(S)-alanyl}-cis,syn-octahydro-1H-indole-2(S)-carboxylic acid.

21. A compound of claim 1 which is 1-{N-[1(S)-carboxy-2-[4-(4-chloro-3-sulfamoylbenzamido)phenyl]ethyl]-(S)-alanyl}-cis,syn-octahydro-1H-indole-2(S)-carboxylic acid.

22. A compound of claim 1 which is 1-{N-[1(S)-carboxy-2-[4-(4-chloro-3-N-methylsulfamoylbenzamido)phenyl]ethyl]-(S)-alanyl}-cis,syn-octahydro-1H-indole-2(S)-carboxylic acid.

23. A compound of claim 1 which is 1-{N-[1(S)-ethoxycarbonyl-3-[4-(4-chloro-3-sulfamoylbenzamido)phenyl]propyl]-(S)-alanyl}-cis,syn-octahydro-1H-indole-2(S)-carboxylic acid.

24. A compound of claim 1 which is 1-{N-[1(S)-ethoxycarbonyl-3-[4-(4-chloro-3-N-methylsulfamoylbenzamido)phenyl]propyl]-(S)-alanyl}-cis,syn-octahydro-1H-indole-2(S)-carboxylic acid.

25. A compound of claim 1 which is 1-{N-[1(S)-ethoxycarbonyl-3-[4-(6-chloro-3,4-dihydro-1,1-dioxo-7-sulfamoyl-2H-1,2,4-benzothiadiazine-3-acetamido)-phenyl]propyl]-(S)-alanyl}-cis,syn-octahydro-1H-indole-2(S)-carboxylic acid.

26. A pharmaceutical composition comprising an antihypertensive effective amount of a compound of claim 1 and a pharmaceutically acceptable carrier.

27. A method of treating hypertension in mammals comprising administering an antihypertensive effective amount of a compound of claim 1 to a mammal in need of such treatment.

* * * * *